United States Patent [19]

Johal et al.

[11] Patent Number: 4,960,697

[45] Date of Patent: Oct. 2, 1990

[54] RECOVERY OF POLYSACCHARIDES BY EMPLOYING A DIVALENT CATION WITH A WATER MISCIBLE ORGANIC SOLVENT

[75] Inventors: Sajit S. Johal, Sagamore Hills; Howard S. Cash, Cleveland Heights, both of Ohio

[73] Assignee: The Standard Oil Company, Cleveland, Ohio

[21] Appl. No.: 294,153

[22] Filed: Jan. 6, 1989

[51] Int. Cl.$^5$ .................... C12R 1/645; C12P 19/04
[52] U.S. Cl. .................... 435/101; 435/262; 435/911
[58] Field of Search .................... 435/101, 911, 262

[56] References Cited

U.S. PATENT DOCUMENTS

| | | |
|---|---|---|
| 3,301,848 | 1/1967 | Holek . |
| 3,759,896 | 9/1973 | Komatsu . |
| 3,785,896 | 1/1974 | Kassor . |
| 3,900,462 | 8/1975 | Komatani et al. .................... 536/127 |
| 4,053,699 | 10/1977 | Cahalan et al. . |
| 4,072,567 | 2/1978 | Yokobayashi et al. . |
| 4,075,405 | 2/1978 | Takahashi et al. . |
| 4,101,435 | 7/1978 | Hasegawa et al. .................... 536/113 |
| 4,109,663 | 8/1978 | Maeda et al. .................... 131/359 |
| 4,143,201 | 3/1979 | Miyashiro et al. .................... 536/1.1 |
| 4,237,266 | 12/1980 | Sugiura et al. . |
| 4,347,146 | 8/1982 | Abdo .................... 252/8.554 |
| 4,357,423 | 11/1982 | Cox et al. . |
| 4,398,023 | 8/1983 | Miyachi et al. .................... 536/1.1 |
| 4,417,415 | 11/1983 | Cysewski et al. .................... 435/101 |
| 4,599,180 | 7/1986 | Vio et al. .................... 252/8.511 |
| 4,667,741 | 5/1987 | Phelps et al. .................... 166/294 |

*Primary Examiner*—Herbert J. Lilling
*Attorney, Agent, or Firm*—Larry W. Evans; Joseph G. Curatolo; Teresan W. Gilbert

[57] ABSTRACT

The instant invention is a process for the recovery of a polysaccharide, in particular a water-soluble glucan comprising adding a divalent cation to a solution containing the solubilized polysaccharide and then adding a water miscible organic solvent to precipitate the polysaccharide from the solution. The polysaccharide is then separated and collected.

10 Claims, No Drawings

RECOVERY OF POLYSACCHARIDES BY EMPLOYING A DIVALENT CATION WITH A WATER MISCIBLE ORGANIC SOLVENT

This application is related to an application filed at the same time Ser. No. 294,250 filed Jan. 6, 1989 relating to recovery of polysaccharides and entitled "Recovery of Glucan By Employing a Divalent Cation at an Alkaline pH".

BACKGROUND OF THE INVENTION

The invention relates to a process for the recovery of solubilized polysaccharides, in particular nonionic glucans from solution. Further, the invention relates to the recovery of polysaccharides by using a divalent cation and a water miscible organic solvent to precipitate the polysaccharides from solution.

Current procedures teach the use of an alcohol such as isopropyl alcohol or acetone for the recovery of nonionic polysaccharides, in particular glucan from fermentation media and other solutions containing the glucan. Generally, the clarified media is concentrated to a flowable viscosity and then precipitated with 50% by volume solvent. The precipitate is drained and then successively treated with higher concentrations of the water miscible organic solvent. This process which requires concentration to reduce media volumes and large quantities of solvent is an expensive, capital intensive procedure.

U.S. Pat. No. 3,759,896 discloses a process to produce polysaccharides with antitumor activity mainly consisting of B-(1→3)-linked D-glucose residue by obtaining culture filtrates of fungi belonging to Ascomycetes, Basidiomycetes and Fungi imperfecti and then purifying the culture filtrate by sequential treatments of acidification, deionization by ion exchange resins and precipitation with a water soluble miscible solvent.

U.S. Pat. No. 4,072,567 discloses a process for producing a water-insoluble glucan by cultivating a Streptococcus microrganism in a liquid medium and recovering the glucan by sedimentation, filtration or seiving. The crude glucan is further processed by dissolving in sodium hydroxide, centrifuging, neutralizing with hydrogen chloride and then washing.

Glucan derivatives have also been produced by reacting water-insoluble B-1,3 glucan with a cyanogen halide to produce water-insoluble carriers, see U.S. Pat. No. 4,075,405.

Xanthomonas gum, an anionic polysaccharide is a fermentation product of the bacteria *Xanthomonas campestris*. The gum is recovered from the fermentation broth by precipitation. Known precipitating agents for the gum are calcium ion combined with an alkaline pH, isopropyl alcohol and a quaternary compound, see U.S. Pat. No. 4,053,699.

It is desirable to find novel methods to recover solubilized polysaccharides from solution. Further, it is desirable to reduce recovery costs of the polysaccharide as an economic improvement for commercializing a process to produce and recover polysaccharides.

Polysaccharides have been used extensively in the chemical, oil, pharmaceutical, food, cosmetic and paper manufacturing industries. The process of the instant invention is useful in that nonionic polysaccharides, in particular glucans are useful as viscosifiers, binders, thickeners and stabilizers in industrial and food applications. Glucans have various industrial applications such as enhanced oil recovery and oil well drilling muds, tablet coatings, opthalmic solutions, antiacid suspensions, porcelain and ceramic glazes, ceramic binders, water-based paints, paper coatings, printing inks, integrated circuit chips, agricultural seed coatings, pesticide sprays and the like.

It is an object of the instant invention to recover nonionic polysaccharides, in particular glucans from solution. It is another object of the instant invention to recover polysaccharides from solution by the addition of a divalent cation in concert with a water miscible organic solvent.

These and other objects, together with the advantages over known methods shall become apparent from the specification which follows and are accomplished by the invention as herein described and claimed.

SUMMARY OF THE INVENTION

The instant invention is a process for the recovery of a nonionic polysaccharide, in particular a water-soluble glucan comprising adding a divalent cation to a solution containing solubilized glucan and then adding a water miscible organic solvent to precipitate the glucan from the solution. The glucan is then separated and collected.

DETAILED DESCRIPTION OF THE INVENTION

The process of the instant invention is to recover nonionic polysaccharides, in particular water soluble glucans from solutions containing the solubilized glucan.

Generally, a glucan is defined as a polysaccharide substance composed of glucose and is characterized by 1-3 linked D-glycosyl units. The glucan recovered by the instant invention is water soluble. Exemplary glucans include but are not limited to scleroglucan, schizophyllan and the like. Scleroglucan and schizophyllan are nonionic polysaccharides which are characterized as a linear chain of 1-3-linked D-glycosyl units with about 30 to about 35 percent of the linear chain containing single D-glycosyl units which are attached by 1-6 linkages. The average molecular weight is greater than or equal to $5 \times 10^6$. They are nonionic homopolysaccharides. The chains are self-associated over a triple helix arrangement. They dissolve in water to form pseudoplastic solutions.

Organisms that produce polysaccharides are filamentous fungi, bacteria and the like.

Typical filamentous fungi that produce polysaccharides, in particular glucan, include but are not limited to organisms belonging to the genus Sclerotium, Sclerotinia, Corticum, Helotium, Stromatinia, Claviceps and the like. Exemplary organisms which produce glucans include but are not limited to *Sclerotium glucanicum, Sclerotium delphinii, Sclerotium coffeicolum, Schizophyllum commune, Sclerotium rolfsii, Corticium rolsii, Sclerotinia gladod, Stromatinia narcissi* and the like. The organisms listed in U.S. Pat. No. 3,301,848 to Halleck and in U.S. Pat. No. 3,759,896 to Komatsu et al. are also included as organisms that excrete glucan. Scleroglucan is produced by filamentous fungi of the genera Sclerotium, in particular by *Sclerotium rolfsii, Sclerotium glucanicum, Sclerotium delphinii, Sclerotium coffeicolum* and the like. Schizophyllan is produced by fungi of the genera Schizophyllum, in particular by *Schizophyllum commune.*

Conventional methods are employed in culturing microorganisms for the production of the extracellular water soluble polysaccharides, in particular glucan. Typical cultivation methods employed include but are not limited to batch, fed batch, semi-continuous fermentation, continuous fermentation and the like. In general, the process involves growing the organism, inoculating a batch of fermentable broth with the organism, allowing the organism to ferment and recovering the water soluble polysaccharide from the broth.

The aqueous nutrient medium should provide a substrate for the production of the polysaccharide by the organism. The aqueous nutrient medium will normally contain assimilable carbon and nitrogen sources, organic materials and if required, minor organic and inorganic nutrients such as trace salts, trace elements, vitamins, amino acids and the like.

The excreted water soluble polysaccharide is then separated from the biomass in the medium by conventional techniques such as centrifugation, filtration and the like.

The present invention is directed toward recovery of the polysaccharide from a solution containing the polysaccharide which may be any solution containing polysaccharide such as fermentation broth. The polysaccharide, in particular water soluble glucan is recovered from solution by adding a divalent cation in concert with a water miscible organic solvent.

The divalent cation is added with mixing to the solution. The addition can take the form of adding a solid, saturated solution or a dilute solution. The divalent cation can be employed either alone or in combination. The divalent cation is preferably divalent cation salts of the divalent metals of calcium, zinc, magnesium, manganese, iron, copper, cobalt and nickel. Exemplary divalent cations include but are not limited to calcium chloride, magnesium chloride, calcium sulfate, manganese chloride, iron chloride, zinc copper, calcium hydroxide and the like. The preferred divalent cations are calcium chloride, magnesium chloride and calcium sulfate. The concentration of the divalent cation ion is in the range from about 0.1% to about 20%, preferably about 0.2% to about 10% and most preferably about 0.5% to about 2% of the volume of the solution.

When a calcium divalent cation is employed, the dissolution and mixing of the calcium divalent cation results in the appearance of an insoluble precipitate which is calcium oxalate, a complex of calcium and oxalic acid. The calcium oxalate is removed from the solution by conventional methods such centrifugation, filtration or the like.

A water miscible organic solvent is then added to the solution. The water miscible organic solvent is added to the solution in the concentration range of about 10% to about 70%, preferably about 20% to about 40%. The water miscible organic solvent can be used alone or in combination. Typical water miscible organic solvents include but are not limited to isopropyl alcohol, acetone, ethanol, methanol, iso-proponal, n-proponal, n-butanol, ether, acetonitrile and the like. The preferred water miscible organic solvents are isopropyl alcohol, ethanol and the like. One or more washes with the water miscible organic solvent are employed to precipitate the polysaccharide.

The precipitated water soluble polysaccharide is collected from the solution by conventional methods such as centrifugation, filtration and the like. The polysaccharide can be further processed and purified by known methods such as rehydration, reprecipitation and the like.

This approach reduces the solvent requirements of the process. The addition of a divalent cation to the glucan solution prior to solvent addition results in a divalent metal-glucan complex which exhibits reduced solubility.

SPECIFIC EMBODIMENTS

The following examples further illustrate the present invention. These embodiments are presented by way of example and not by way of limitation of the scope of the invention. Further, it is understood that variations and modifications can be made by one skilled in the art without departing from the spirit and the scope of the invention.

EXAMPLE 1

About 10 mls of clarified scleroglucan broth having a viscosity of about 753 cps at about 10.2 sec. −1 and about 0.5% glucan concentration was pipetted into five separate test tubes and the following five treatments were performed respectively to the samples.

SAMPLE 1. About 1% $CaCl_2$ was mixed with the broth and centrifuged at 12,000 rpm for 10 min. to remove the oxalic acid. Then about 5 mls of isopropanol was added to the supernatant and after about 10 min. the precipitated glucan was collected by spooling onto a pipet. The volume of the remaining liquid was measured.

SAMPLE 2. About 1% $CaCl_2$ was mixed with the broth and then centrifuged at 12,000 rpm for 10 min. as in sample 1. Then about 10 mls of isopropanol was added to the supernatant and after about 10 min. the glucan precipitated out and was then collected on a pipet by spooling. The volume of the remaining liquid was measured.

COMPARATIVE SAMPLE 3. About 5 mls of isopropanol was added to the broth and after about 10 min. the precipitated glucan was then collected by spooling and the volume of the remaining liquid measured.

COMPARATIVE SAMPLE 4. About 10 mls of isopropanol was added to the scleroglucan broth and after about 10 min. the glucan precipitated out and was then collected by spooling onto a pipet. The volume of the remaining liquid was measured.

COMPARATIVE SAMPLE 5. About 20 mls of isopropanol was added to broth and after about 10 min. the precipitated glucan precipitated out and was then collected by spooling onto a pipet. The volume of the remaining liquid was noted.

Scleroglucan precipitated in all samples, however, the morphology and water content of the precipitates differed. A determination of this can be made by measuring the volume of remaining solution. The results are presented in Table 1 with increasing scleroglucan concentration even lower solvent concentrations can be employed. This demonstrates that employing a divalent cation with a water miscible organic solvent produces a more compact, concentrated scleroglucan precipitate which holds less agueous solvent. The tighter, lower solvent content precipitate which facilitates separation and recovery of the biopolymer.

| Treatment | $CaCl_2$ Conc. | Isopropanol Conc. (%) | Liquid Recovered after Removing Precipitate (m/s) | Liquid Recovered (%) |
|---|---|---|---|---|
| 1 | 1% | 33 | 8.05 | 54 |
| 2 | 1% | 50 | 12.65 | 63 |

-continued

| Treatment | CaCl$_2$ Conc. | Isopropanol Conc. (%) | Liquid Recovered after Removing Precipitate (m/s) | Liquid Recovered (%) |
|---|---|---|---|---|
| 3 | 0% | 33 | 4.95 | 33 |
| 4 | 0% | 50 | 10.05 | 50 |
| 5 | 0% | 67 | 22.75 | 76 |

EXAMPLE 2

About 5 mls of clarified fermentation broth containing greater than 1,000 ppm of glucan was pipetted into four separate test tubes. Sufficient CaCl$_2$ from about a 50% CaCl$_2$ stock solution was added to the sample tubes so that CaCl$_2$ concentrations of 1%, 2%, 3%, and 4% were attained respectively. The samples were vortexed for about 1 to 2 min. and then centrifuged at about 17,500 X g for about 10 min., after which the supernatant containing glucan was retained and the pellet of calcium oxalate discarded.

About 2.5 mls of ethanol was added to each of the test tubes containing the various CaCl$_2$ concentrations. The test tubes were then vortexed and within a few seconds a precipitate of glucan was obtained and the viscosity of the solution declined to that of water.

This example was also performed substituting KCl for the CaCl$_2$ and a precipitated glucan gel was also obtained.

We claim:

1. A process for the recovery of nonionic glucan which is produced from filamentous fungi selected from the group consisting of the genera *Sclerotium, Sclerotinia, Corticum, Helotium, Stromatinia, Schizophyllum,* and *Calviceps* which are cultured in culture medium, extracellular glucan is excreted into the culture medium by the fungi comprising (1) adding a divalent cation wherein the divalent cation is in the range from about 0.1% to about 20% of the volume of the solution and is a divalent cation salt of a divalent metal of calcium zinc, magnesium, manganese, iron, copper, colbalt, nickel and combinations thereof, to a solution containing solubilized nonionic glucan and (2) then adding a water miscible organic solvent wherein the water miscible organic solvent is added to the solution in the concentration range of about 10% to about 70% and selected from the group consisting of isopropyl alcohol, acetone, ethanol, methanol, iso-proponal, n-proponal, n-butanol, ether, acetonitrile and combinations thereof resulting in the precipitation of the glucan from solution.

2. The process of claim 1 wherein the filamentous fungi are selected from the group consisting of *Sclerotium glucanicum, Sclerotium delphinii, Sclerotium coffeicolum, Schizophyllum commune, Sclerotium rolfsii, Corticum rolsii, Sclerotinia gladod,* and *Stromatinia narcissi.*

3. The process of claim 1 wherein the filimentous fungi are selected from the group consisting of *Sclerotium rolfsii, Sclerotium glucanicum, Sclerotium delphinii, Sclerotium coffeicolum* and *Schizophyllum commune.*

4. The process of claim 1 wherein the divalent cation is selected from the group consisting of calcium chloride, magnesium chloride, calcium sulfate, manganese chloride, iron chloride, zinc copper, calcium hydroxide and combinations thereof.

5. The process of claim 1 wherein the divalent cation is selected from the group consisting of calcium chloride, magnesium chloride, calcium sulfate and combinations thereof.

6. The process of claim 1 wherein the divalent cation is in in the range from about 0.2% to about 10% of the volume of the solution.

7. The process of claim 1 wherein the divalent cation is in in the range from about 0.5% to about 2% of the volume of the solution.

8. The process of claim 1 wherein the water miscible organic solvent is added to the solution in the concentration range of about 20% to about 40%.

9. The process of claim 1 wherein a single wash of water miscible organic solvent precipitates the glucan in solution.

10. The process of claim 1 wherein more than one wash of water miscible organic solvent is employed to recover the glucan from solution.

* * * * *